US011276384B2

(12) United States Patent
Woodruff et al.

(10) Patent No.: US 11,276,384 B2
(45) Date of Patent: Mar. 15, 2022

(54) AMBIENT SOUND ENHANCEMENT AND ACOUSTIC NOISE CANCELLATION BASED ON CONTEXT

(71) Applicant: Apple Inc., Cupertino, CA (US)

(72) Inventors: John Woodruff, Santa Cruz, CA (US); Tom-Davy W. Saux, Los Altos, CA (US); Vladan Bajic, San Francisco, CA (US); Vasu Iyengar, Pleasanton, CA (US); Andrew E. Greenwood, San Francisco, CA (US); Tyrone T. Chen, San Jose, CA (US); Jakub Mazur, Santa Clara, CA (US); Tony S. Verma, San Francisco, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 16/871,661

(22) Filed: May 11, 2020

(65) Prior Publication Data

US 2020/0380945 A1 Dec. 3, 2020

Related U.S. Application Data

(60) Provisional application No. 62/855,333, filed on May 31, 2019.

(51) Int. Cl.
*G10K 11/178* (2006.01)

(52) U.S. Cl.
CPC .... *G10K 11/178* (2013.01); *G10K 2210/1081* (2013.01)

(58) Field of Classification Search
CPC ..... A61F 11/06; G10K 11/175; G10K 11/178; G10K 2210/1081; H04R 1/1008;
(Continued)

(56) References Cited

U.S. PATENT DOCUMENTS 8,358,799 B1 * 1/2013 Gresko ................ H04R 1/1091 381/371
8,515,089 B2 8/2013 Nicholson
(Continued)

FOREIGN PATENT DOCUMENTS

CN 104871557 8/2015
CN 104918177 9/2015
(Continued)

OTHER PUBLICATIONS

Kuk, Francis, "Selecting the Right Compression", Audiology Online, retrieved from the Internet <https://www.audiologyonline.com/articles/selecting-the-right-compressoin-18120>, Sep. 19, 2016, 22 pages.

(Continued)

*Primary Examiner* — Vivian C Chin
*Assistant Examiner* — Friedrich Fahnert
(74) *Attorney, Agent, or Firm* — Womble Bond Dickinson (US) LLP

(57) ABSTRACT

An audio system has an ambient sound enhancement function, in which an against-the-ear audio device having a speaker converts a digitally processed version of an input audio signal into sound. The audio system also has an acoustic noise cancellation (ANC) function that may be combined in various ways with the sound enhancement function, and that may be responsive to voice activity detection. Other aspects are also described and claimed.

10 Claims, 6 Drawing Sheets

(58) Field of Classification Search
CPC ................ H04R 1/1016; H04R 1/1083; H04R 2430/01; H04R 2460/01
USPC ........................................ 381/71.6, 71.11, 74
See application file for complete search history.

(56) References Cited

U.S. PATENT DOCUMENTS

| | | | |
|---|---|---|---|
| 9,825,598 B2 | 11/2017 | Kraft et al. | |
| 9,886,954 B1 | 2/2018 | Meacham et al. | |
| 10,034,092 B1 | 7/2018 | Nawfal et al. | |
| 10,074,354 B2 | 9/2018 | Gauger, Jr. et al. | |
| 10,102,843 B1 | 10/2018 | Le et al. | |
| 2014/0079235 A1 | 3/2014 | Lyons | |
| 2014/0169579 A1* | 6/2014 | Azmi | G10K 11/17821 381/71.6 |
| 2015/0071453 A1* | 3/2015 | Po | G10K 11/17854 381/71.11 |
| 2015/0170645 A1 | 6/2015 | Di Censo et al. | |
| 2015/0222977 A1* | 8/2015 | Angel, Jr. | H04R 1/105 381/74 |
| 2016/0081595 A1 | 3/2016 | Hui et al. | |
| 2017/0194020 A1 | 7/2017 | Miller et al. | |
| 2017/0345408 A1 | 11/2017 | Hong et al. | |
| 2018/0097495 A1 | 4/2018 | Kok et al. | |
| 2019/0116430 A1 | 4/2019 | Schnell et al. | |
| 2019/0268686 A1 | 8/2019 | Degraye et al. | |
| 2020/0357374 A1* | 11/2020 | Verweij | H04S 7/304 |

FOREIGN PATENT DOCUMENTS

| | | |
|---|---|---|
| CN | 105814913 | 7/2016 |
| CN | 108475502 | 8/2018 |
| JP | 2015-173369 | 10/2015 |
| JP | 2017-507550 | 3/2017 |
| JP | 2018-157484 | 10/2018 |

OTHER PUBLICATIONS

Examination Report for Australian Application No. 2020203567 dated Nov. 6, 2020, 13 pages.

Extended European Search Report for European Application No. 20175819.0 dated Oct. 6, 2020, 10 pages.

Non-Final Office Action for U.S. Appl. No. 16/871,885 dated Dec. 16, 2020, 26 pages.

Serizel, Romain, et al., "Integrated Active Noise Control and Noise Reduction in Hearing Aids", IEEE Transactions on Audio, Speech, and Language Processing, vol. 18, No. 6, Aug. 2010, pp. 1137-1146.

Notice of Preliminary Rejection for Korean Application No. 10-2020-0064167 dated Mar. 31, 2021, 9 pages.

Notification of Reasons for Refusal for Japanese Application No. 2020-094512 dated May 27, 2021, 7 pages.

Notification of First Office Action and Search Report for Chinese Application No. 202010472896.9 dated Dec. 3, 2021, 22 pages.

Decision for Refusal for Japanese Application No. 2020-094512 dated Jan. 31, 2022, 4 pages.

* cited by examiner

AMBIENT SOUND ENHANCEMENT AND ACOUSTIC NOISE CANCELLATION BASED ON CONTEXT

This non-provisional patent application claims the benefit of the earlier filing date of U.S. provisional application No. 62/855,333 filed May 31, 2019.

FIELD

An aspect of the disclosure here relates to digital audio signal processing techniques for automatically controlling how ambient sound is reproduced by an against-the-ear hearing device, such as a headphone or a mobile phone handset, in accordance with a context of the user of the device. Other aspects are also described.

BACKGROUND

Consumer electronic devices referred to as against-the-ear hearing devices, such as headphones and mobile phone handsets, are used in a variety of different ambient sound environments and are worn and then removed by their user quite often. The listening experience of users of these devices may be affected by changing ambient sound environments.

SUMMARY

An aspect of the disclosure here relates to an audio system that has an ambient sound enhancement function, also referred to here as a transparency mode of operation, in which an against-the-ear audio device having one or more speakers converts a digitally processed version of an input audio signal into sound. In one aspect, the reproduced ambient sound may be louder as compared to the user hearing the ambient sound without the device against their ear, due to amplification that may be in accordance with a stored hearing profile of the user. When the ambient sound enhancement function is active, the input audio signal contains ambient or environmental sound pick up from one or more microphones in the device; in a "playback" situation, the input audio signal is a combination signal that also contains program audio, such as music, the voice of a far end user during a phone call, or the voice of a virtual assistant program. When the ambient sound enhancement function is inactive, the input audio signal may contain program audio but not ambient sound pick up.

In one aspect, while reproducing the ambient sound according to a frequency dependent "transparency" gain that may or may not be set according to the hearing profile of the user, a digital processor (configured as an ambient sound environment analyzer or noise profile analyzer) detects that the ambient sound changes from quiet to loud (e.g., its sound pressure level rises above a threshold.) In response, the processor reduces the transparency gain (where this reduction may or may not be in accordance with the hearing profile of the user.) This automatic reduction in level of the reproduced ambient sound may reduce distortion or maintain a comfortable sound level in certain situations, such as when the user enters a significantly louder sound environment (e.g., a restaurant or a social club.) If the against-the-ear device can produce anti-noise for acoustic noise cancellation (ANC), then in that case the processor could raise a level of the produced anti-noise in a low frequency band (where ANC is more effective) in response to detecting that the ambient sound changes from quiet to load. That may mitigate the occlusion effect in the low frequency band. Also, the reduction in the frequency dependent transparency gain may be limited to a high frequency band where ANC is less effective. Since a majority of the anti-noise is in the low frequency band and not in the high frequency band, raising the anti-noise does not turn down the high frequency band. As a result, the reproduced ambient sound in the high frequency band would sound too loud but for the reduction in the frequency dependent transparency gain. Such automatic control of the ambient sound enhancement function results in a more desirable user experience as the audio system automatically adapts to changing ambient sound environments, and to the frequent donning and removal of the against the ear audio device being for example a headphone or a mobile handset.

In another aspect here, the processor starts producing anti-noise or raises a level of existing anti-noise being produced in the low frequency band, in response to detecting a louder ambient sound environment, but without necessarily reducing the transparency gain in the high frequency band (for reproducing the ambient sound.)

In yet another aspect, the ambient sound is reproduced (in accordance with the hearing profile of the user) with more gain in a high frequency band than in a low frequency band, while producing anti-noise whose level is greater in the low frequency band than in the high frequency band.

Another aspect of the disclosure here is how to control ANC during ambient sound enhancement, in order to improve intelligibility of speech in the ambient sound environment. In that aspect, while reproducing the ambient sound (which may or may not be in accordance with the user's hearing profile), the processor detects speech in the ambient sound. So long as no speech is being detected, the anti-noise continues to be produced (while reproducing the ambient sound), but whenever speech is detected the anti-noise level is lowered. This helps make the speech (that is present in the reproduced ambient sound) more easily heard or more intelligible. This response (lowering the anti-noise during speech intervals and raising it back up during non-speech) may be fast acting, e.g., may vary on a per audio frame basis and per frequency bin and may conform to psychoacoustics.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Consumer electronic devices referred to as against-the-ear hearing devices, such as headphones and mobile phone handsets, are used in a variety of different ambient sound environments. For instance, consider a user who is at a train station and is wearing a headset. While waiting for a train to arrive the user could be talking to a friend standing next to them when the train arrives and creates the typically loud train sound. The headset occludes the user's ear and therefore passively attenuates the voice of the friend. If the headset has an ambient sound enhancement function, where the ambient sound is being actively reproduced at the user's ear (optionally according to the user's hearing profile), then it will allow the friend's speech to be heard more easily. The arrival of the train however will result in the train sound also being reproduced and in some cases amplified (according to the user's hearing profile), thereby making it difficult for the user to hear the friend's speech. In another example, the user (while wearing the headset or holding the mobile handset again their ear) is walking with their friend to a local social club or restaurant, and upon entering will hear an undesirable, significant increase in babble noise (being reproduced by the ambient sound enhancement function.) The same ambient sound environment is also heard differently by different users of the system, as some users have lower dynamic range in their hearing than others such that soft or quiet sounds are barely heard by those particular users. A further problem that is especially apparent with certain headphones is the occlusion effect (body conducted sound such as the user's own voice becomes trapped in the ear canal that is blocked by the headphone.) A desirable audio system may also be one that can automatically adapt to such changing ambient sound environments, and to the frequent donning and removal of the headphone or mobile handset, in order to provide a more pleasing hearing experience to the user.

Figure 1:
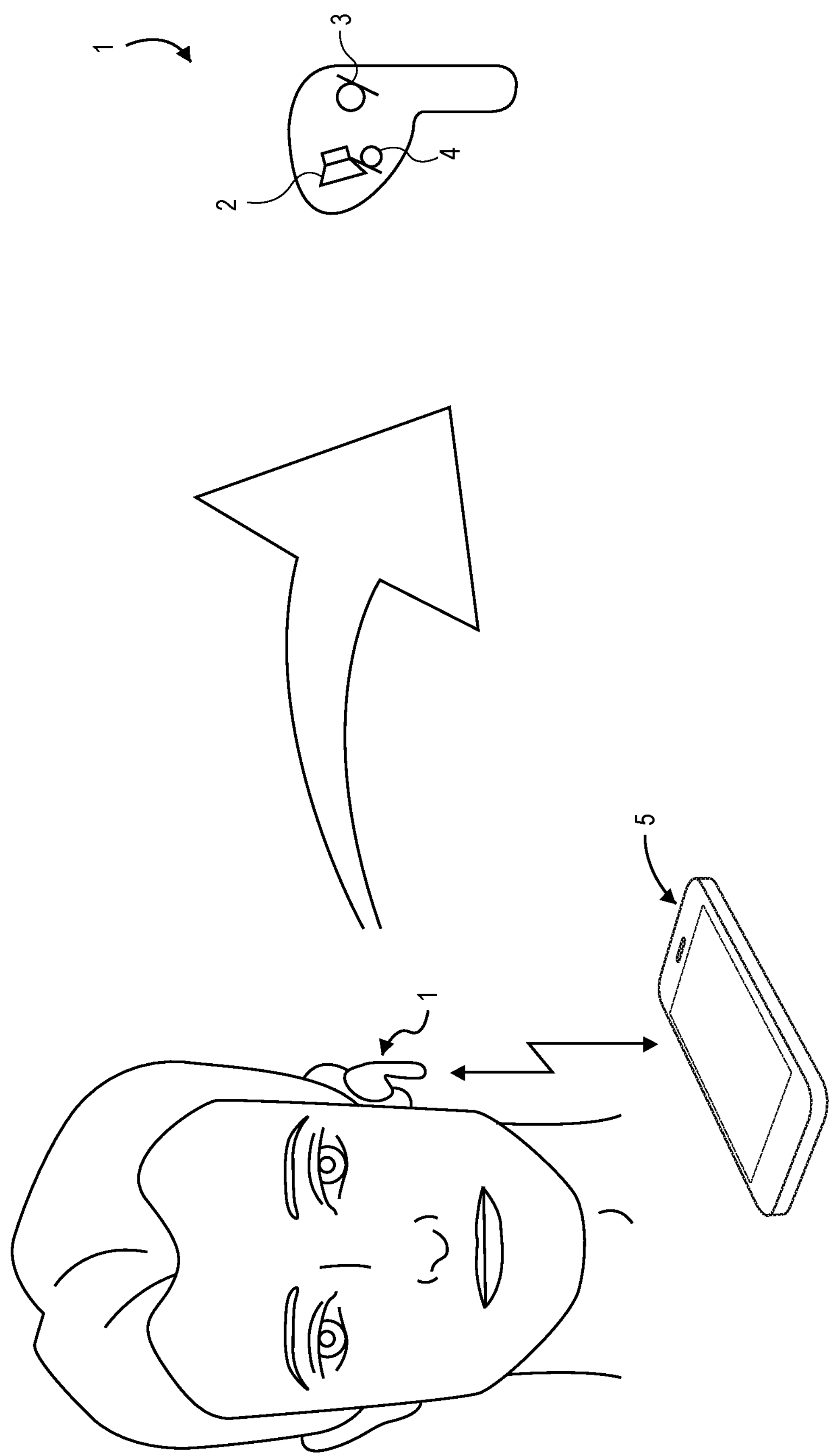
FIG. 1 shows an example against-the-ear device.

FIG. 1 shows an example of an against-the-ear device 1 that is part of an audio system in which a method for personalized ambient sound enhancement can be implemented. The against-the-ear device 1 shown is an in-ear earbud (in-ear headphone which may be a sealing-type that has a flexible ear tip, or it may be non-sealing or loose fitting type), which may be one of two headphones (left and right) that make up a headset. The methods described below for personalized sound enhancement can be implemented for one or both of the headphones that make up a headset. Alternatives (not shown) to the in-ear earbud include an on-the-ear headphone, an over-the-ear headphone, and a mobile phone handset. The against-the-ear device 1 is shown in use, by its user (who may also be referred to as a listener or a wearer.) The against-the-ear device 1 has an against-the-ear acoustic transducer or speaker 2 (arranged and configured to reproduce sound directly into an ear of a user), an external microphone 3 (arranged and configured to receive ambient sound directly), and an internal microphone 4 (arranged and configured to directly receive the sound reproduced by the speaker 2.) These may all be integrated in a housing of the against-the-ear device, along with the transducers and the electronics that process and produce the transducer signals (output microphone signals and an input audio signal to drive the speaker 2.). The electronics may include an audio amplifier to drive the speaker 2 with the input audio signal, a microphone sensing circuit or amplifier that receives the microphone signals converts them into a desired format for digital signal processing, and a digital processor and associated memory, where the memory stores instructions for configuring the processor (e.g., instructions to be executed by the processor) to perform digital signal processing tasks discussed below in more detail. Such electronics may reside in one or both headphone housings of the headset, or elsewhere in the headset. Note it is possible that some or essentially all of such electronics reside in another device, separate from the against-the-ear device 1, such as in an audio source device 5 as depicted in FIG. 1. For instance, in the case of the against-ear-device 1 being a left headphone or right headphone, the headphone may be connected to the audio source device 5 shown in the example of FIG. 1 as a smartphone. The connection may be a wired connection (e.g., one that provides power or an amplified analog audio signal to drive the speaker 2, in which case there may be no need for a power source in the headphone housing) or a wireless connection (e.g., a BLUETOOTH link.) In both cases, the connection to the audio source device 5 is used to provide the input audio signal to drive the speaker 2, or to provide the microphone signals (from the external and internal microphones of the headphone) to the processor and memory in the audio source device 5.

There are many instances where a user, while wearing an against-the-ear device 1, may have a preference or need for hearing at a higher sound pressure level, SPL, than would the average person. To meet the preference or need of such a user, the ambient sound could be amplified by the audio system in accordance with a hearing profile of the user (e.g., a data structure stored in memory), and reproduced through the speaker 2 as an ambient sound enhancement function. This may be performed without any anti-noise being produced by an acoustic noise cancellation, ANC, function. If the user, while wearing the headset or holding the smartphone against their ear, then enters a social club that has a much louder ambient sound level, the amplified sound may appear (be heard as) distorted or uncomfortably loud. The audio system should automatically reduce the reproduced ambient sound level in such a condition, based on the wearer's hearing profile and based on the ambient sound level. And as described below, the audio system may also take advantage of an available ANC function in that case, by activating or increasing the anti-noise level to cancel the elevated levels of leaked ambient sound.

Figure 2:
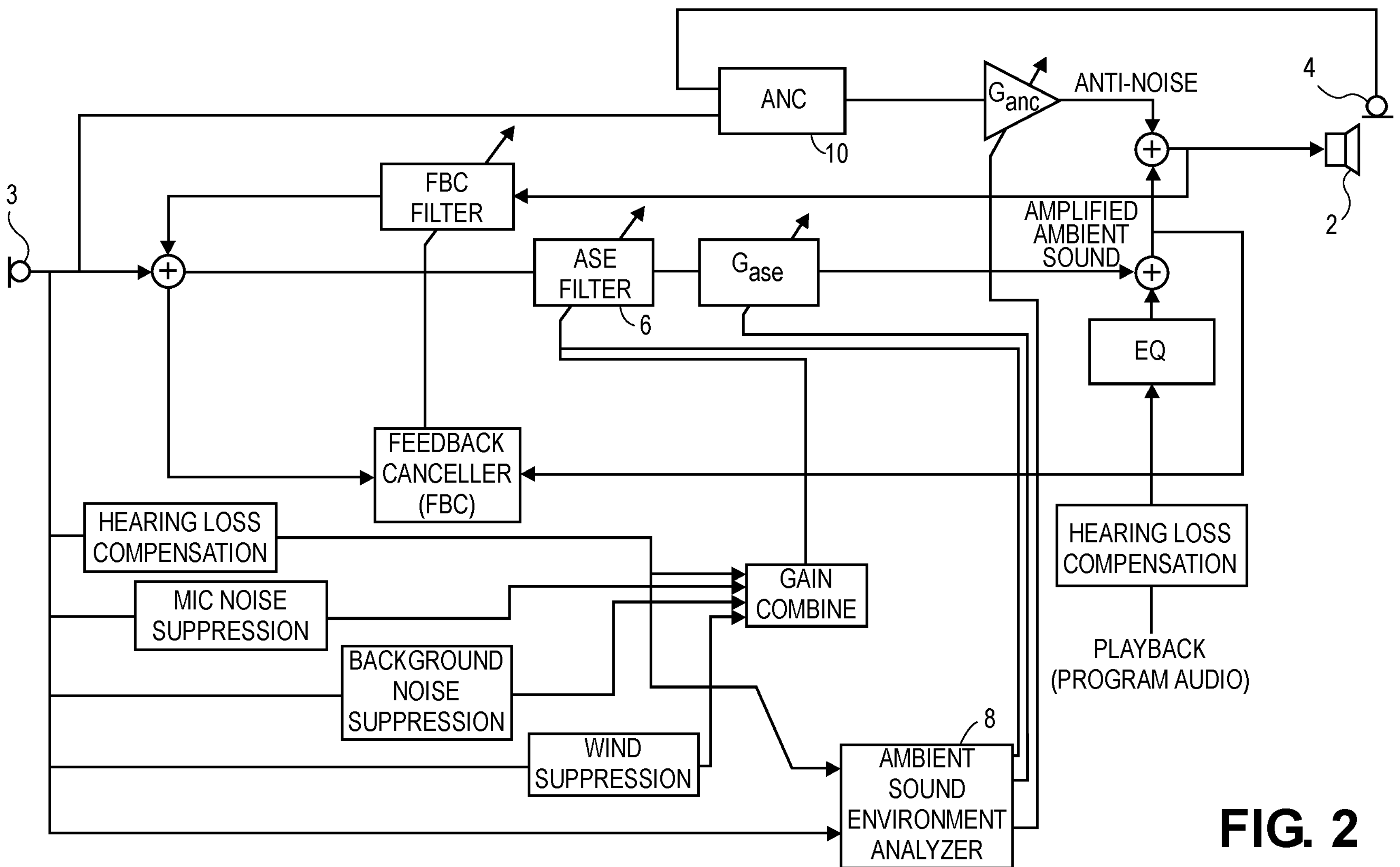
FIG. 2 is a block diagram of an audio system that combines ambient sound enhancement and acoustic noise cancellation for an against the ear device.

Turning now to FIG. 2, this is a block diagram of an audio system that combines personalized ambient sound enhancement and acoustic noise cancellation for a user of the against the ear device 1. The elements of the audio system shown in FIG. 2 and described below that perform digital signal processing may all be implemented as one or more programmed digital processors (generically referred to here as a "a processor" that is to execute instructions stored in memory.) Ambient sound in an acoustic environment of a user who is wearing (using) the against the ear audio device 1 is picked up by the external microphone 3. Its output, digitized microphone (audio) signal is then filtered by an ASE filter 6. The transfer function of the ASE filter 6 is time-varying, e.g., on a frame by frame basis where each audio frame may include 10-100 milliseconds of the microphone signal, and may be set by a gain combine process. The gain combine process combines information from various detectors, to determine the transfer function of the ASE filter 6. These detectors may provide information about one or more of the following: the sound pickup channel (microphone noise characteristics in the mic suppression block); the ambient sound environment (background noise estimates made by a background noise suppression block and wind noise estimates made by a wind suppression block); and the hearing profile of the user (hearing loss compensation block.) Such information is then used by the gain combine process, to determine how to configure the ASE filter 6 so as to spectrally shape the ambient sound pickup channel at the input of the ASE filter 6. The ASE filter 6 may be composed of a cascade of digital filters that spectrally shape the ambient sound pickup channel for purposes of different types of noise suppression, e.g., microphone noise, background noise, and wind. In addition, the cascade of digital filters may include blocks that perform dynamic range compression and spectral shaping that are tuned for compensating the user's hearing loss.

As used herein, the "hearing profile" defines the hearing needs and preferences of the user including hearing level or hearing loss, as dB HL, across various frequencies of interest within the range of normal human hearing (also referred to here as auditory sub-bands.) The hearing profile may additionally specify quiet, comfortable and loud listening levels, frequency-dependent amplification preferences across different types of audio content (e.g., voice phone call, podcast, music, movies) or the user's sensitivity to noise or sound processing artifacts. The hearing profile may be derived from for example a stored audiogram of the user and may include outcomes of other standard hearing evaluation procedures such as Speech-in-Noise testing or measurement of otoacoustic emissions. In addition, or as an alternative to objective hearing evaluations such as the audiogram, the hearing profile may be the result of a process that generates acoustic stimuli using the speakers in the against-the-ear audio device and monitors or evaluates the user's responses to those acoustic stimuli (e.g., as verbal responses that have been picked up by a microphone of the audio device, or as manual responses entered by the user through a graphical user interface of the audio system.) The hearing profile may thus define the hearing preference or hearing sensitivity of the user, for example in terms of hearing level in dB (dB HL).

Here it should be noted that while the figures show a single microphone symbol in each instance (external microphone 3 and internal microphone 2), as producing a sound pickup channel, this does not mean that the sound pickup channel must be produced by only one microphone. In many instances, the sound pickup channel may be the result of combining multiple microphone signals, e.g., by a beamforming process performed on a multi-channel output from a microphone array.

The ambient sound as picked up in a sound pickup channel (e.g., a microphone signal from the external microphone 3) is filtered in a frequency-dependent transparency gain block Gase, which is controlled by an ambient sound environment analyzer 8 according to the hearing profile of the user (based on input from the hearing loss compensation block.) The ambient sound content is then combined with a playback signal which contains program audio. The program audio may be music, the voice of a far end user during a phone call, or the voice of a virtual assistant program, which has not yet been converted to sound in the ambient environment. This combined audio signal then drives the speaker 2, thereby reproducing the ambient sound (and optionally program audio, if present.) Note that when the ambient sound enhancement function is inactive, e.g. the combined audio signal at the output of the gain block Gase is essentially zero, the input audio signal that drives the speaker 2 may contain program audio but not ambient sound pick up.

When the ambient sound enhancement function is active (the ambient sound is being reproduced, as described above), the ambient sound environment analyzer 8 may detect that the ambient sound environment changes from quiet to loud. A noise profile analyzer, an automatic sound event detector, or a sound environment detector (any of which may be based on a machine learning model) may be used for this purpose, to distinguish between a loud environment and a quiet or active talker environment. The loud environment may, for example, be one where the SPL is above a threshold, such that the audio system should perform an active earplug function to reduce the SPL at the user's ears to more comfortable levels. The quiet or active talker environment is one which may call for the sound enhancement function to be activated, so that speech in the ambient environment may reproduced in a more intelligible manner. In response to detecting that the ambient sound environment changes from quiet to loud, the analyzer 8 signals the Gase gain block to reduce its gain, and it may do so in accordance with a hearing profile of the user (information from the hearing loss compensation block). At that point therefore, the ambient sound is being reproduced in accordance with the reduced gain of Gase, where that gain reduction may also have been determined as a function of the hearing profile of the user.

The changes made to Gase may be slow (in contrast to changes made to the ASE filter 6.) For example, changes to Gase might occur no faster than once per second, e.g., requiring a few seconds to change between one setting and another, as the user leaves a quiet office and walks outside, and then walks into a relatively loud restaurant or social club, or into a bus or a train station (where an arriving train makes for a loud environment.) This also means that the decision to reduce Gase (including any signal processing of the microphone signals needed to make such a decision) may be made by software executing in a separate device, e.g., an application program or an operating system executing in a companion device such as a smartphone, tablet, or laptop computer, which has more computing resources than the against the ear device being for example a wireless earbud. In addition, the decision to reduce Gase may also be based on receiving and processing sensor signals (e.g., a microphone signal, an ambient light sensor output) from a smartwatch that is also worn by the user.

In a basic implementation, the ambient sound environment analyzer 8 may simply compute SPL as derived from the signal from the external microphone 3, and then monitors the SPL; when the SPL drops below a threshold, it may respond by signaling that Gase be reduced, based on for example having consulted a look up table that was previously prepared based on the hearing profile of the user. A more complex implementation of the analyzer 8 may be a machine learning model that receives as input SPL measurements that were made at several different frequency bands, and has been trained to evaluate the noise profile in its input SPL measurements to output a Gase value (also referred to here as a tuning setting) for the Gase gain block. In most instances, the analyzer 8 would be configured to output one of at least two different tuning settings for Gase, when responding to changes in the ambient sound environment; a practical implementation is expected to have finer granularity, with more than two tuning settings for the Gase gain block.

Still referring to FIG. 2, the audio system may also have an acoustic noise cancellation, ANC, block 10 that enables the against-the-ear audio device to produce anti-noise for acoustic noise cancellation. The anti-noise delivered into the user's ear may mitigate some of the occlusion effect (caused by the against-the-ear device blocking the ear.) The ANC block 10 produces an anti-noise signal while the ambient sound enhancement function is active: the anti-noise signal is combined with the ambient sound signal before they together drive the speaker 2 of the against the ear audio device. The ANC block 10 is shown in this example as being based on a hybrid feedforward and feedback algorithm (using input from both the external microphone 3 (also referred to as the reference microphone) and the internal microphone 4 (also referred to as the error microphone.) In other instances, the ANC block 10 may be feedforward-only ANC.

The audio system combines the benefits of ANC with the ambient sound enhancement function to reduce occlusion effect at low frequencies and personalize the ambient sound enhancement at high frequencies, as follows. In response to detecting that the ambient sound changes from quiet to loud, the analyzer 8 signals a Ganc block to raise the level of the produced anti-noise (during reproduction of the ambient sound.) The Ganc block may be a scalar (wideband) gain block. Raising the level of the anti-noise mitigates the occlusion effect. Similar to the changes in Gase, changes in the level of the anti-noise (by the Ganc block) are performed no faster than once per second. The audio system thus combines this adjustment, namely an increase in Ganc which boosts only a low frequency band due to the nature of ANC, with a reduction in Gase in a high frequency band and not in the low frequency band (the low and high frequency bands do not overlap.)

Figure 3:
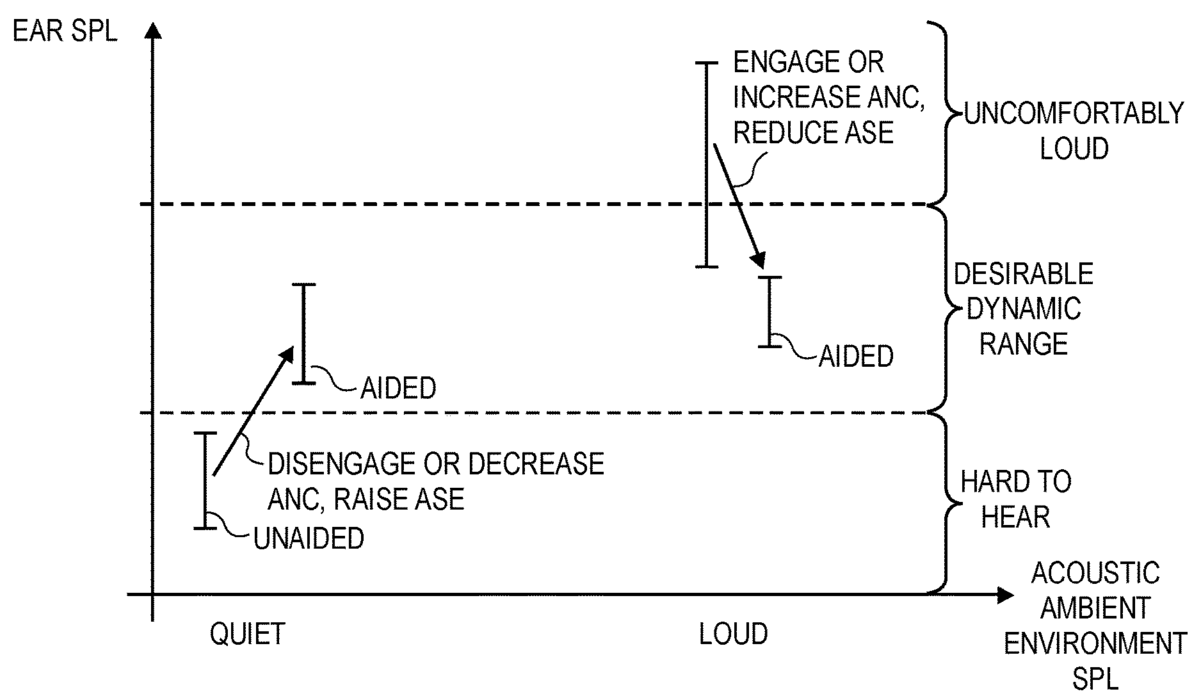
FIG. 3 depicts an example of how sound pressure level, SPL, is managed by the audio system in quiet and loud environments.

An effect of the combining the ANC and ambient sound enhancement functions as described above may be that while the ambient sound is loud, dynamic range of a combination of the reproduced ambient sound and the anti-noise becomes smaller when the anti-noise starts or when the level of existing anti-noise is raised. Since a majority of the anti-noise is in a low frequency band, this may cause the reproduced ambient sound in the high frequency band to be perceived by the user as too loud but for the gain reduction in Gase. FIG. 3 illustrates an example of how SPL is managed in this manner, by the audio system, in quiet and loud environments. The figure shows the expected changes in dynamic range of the ear SPL. When the user is in a quiet ambient environment and is unaided (personalized ambient sound enhancement is disengaged where Gase is "small", and ANC is either disengaged or Ganc is "small"), the ear SPL is in the hard to hear range. To raise the ear SPL in that situation, Gase is automatically increased ("large"), while ANC remains disengaged or Ganc remains small. When the user then moves into a loud ambient, the ear SPL becomes uncomfortably loud initially but then is automatically brought down into a desirable dynamic range by reducing Gase and either engaging ANC or raising Ganc ("large").

Figure 4:
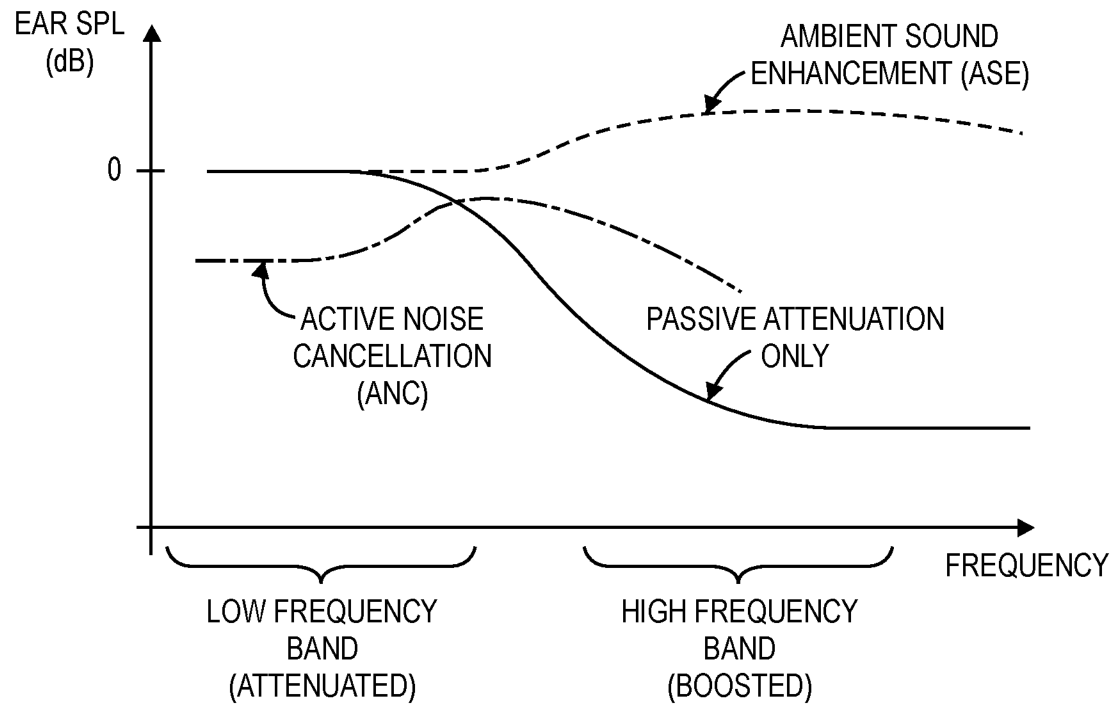
FIG. 4 is a graph or plot of SPL vs. frequency, showing aspects of the audio system that combine to shape how the user hears their ambient environment.
Figure 5:
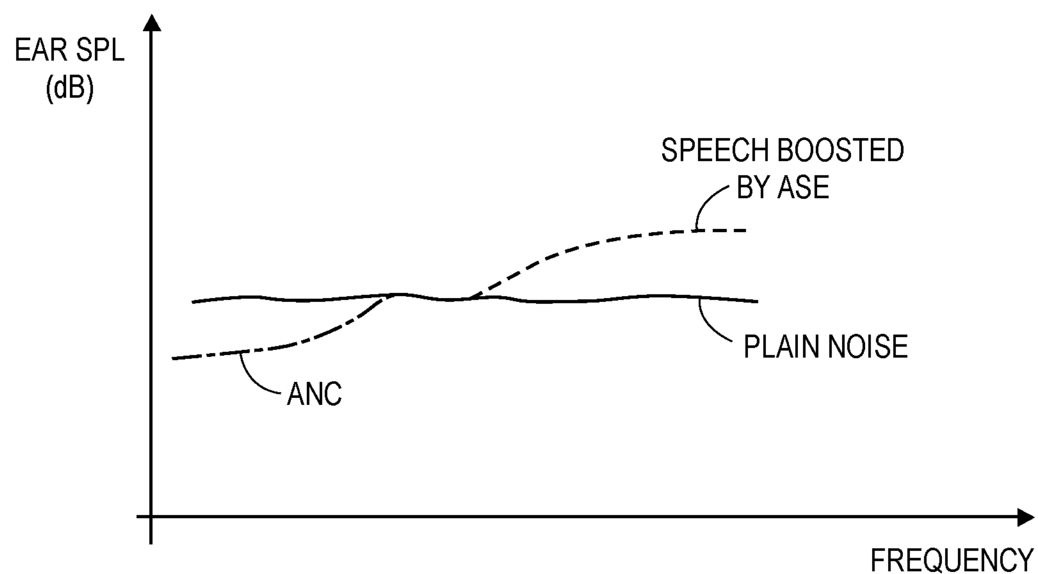
FIG. 5 is a graph that illustrates a plain noise curve versus frequency in a sound pickup channel, and a result where the noise is being cancelled by ANC at low frequencies, superimposed with an instance of speech at high frequencies that has been boosted by the ambient sound enhancement function.

FIG. 4 is a graph or plot of ear SPL vs. frequency, showing three responses of the against-the-ear device of the audio system that combine to shape how the user hears their ambient environment. A first SPL curve ("passive attenuation only") represents the response that is due only to passive attenuation by the against the ear device, in the absence of ANC and ambient sound enhancement. The low frequency band may be a reference set to 0 dB, while at high frequencies (above a transition or knee frequency) the SPL rolls off at the transition frequency and may then level off at some negative dB in the high frequency band. A second SPL curve ("ambient sound enhancement response") represents just the response of a personalized ambient sound enhancement function, which boosts SPL (positive dB) in the high frequencies starting at the transition frequency (remains above 0 dB in the entire high frequency band). The boosted high frequency band enables the ambient to be heard more easily. A third SPL curve represents just the response of the ANC function, which attenuates the SPL (negative dB) in the low frequencies, below the transition frequency. FIG. 5 is a graph that illustrates the combined effect of these three responses, using the example of a plain noise curve versus frequency in a sound pickup channel in the user's ear, e.g., pickup by internal microphone 4—see FIG. 2.) It can be seen how in the low frequency band, the ear SPL exhibits attenuation (of the noise curve) due to acoustic noise cancellation by the ANC function, superimposed with an instance of speech at high frequencies that has been boosted by the personalized ambient sound enhancement function.

Another aspect of the disclosure here is a method performed by an audio system for speech-aware sound enhancement by an against the ear audio device, where the device can produce anti-noise for acoustic noise cancellation, ANC. In such a method, ambient sound is amplified and reproduced by the against the ear audio device in accordance with a hearing profile of the user of the against the ear audio device. The ambient sound is the sound that is in an acoustic environment of the against the ear audio device and as such may be heard by the user. While reproducing the ambient sound, the processor detects speech in the ambient sound (e.g., via voice activity detection, VAD, operating upon the external microphone signal). While reproducing the ambient sound, the against the ear device also produces anti-noise; it does that so long as no speech is detected in the ambient sound; whenever speech is detected, it reduces a level of the produced anti-noise. This enables the user to better perceive the speech in the reproduced ambient sound.

Such a response (reducing the level of the anti-noise, even to the point of deactivating ANC) is a relatively fast acting response, i.e., faster than the transitions described above that respond to changes in detected ambient sound level (between quiet and loud.) The speech-responsive changes to the ANC function may conform to psychoacoustics, and may be on a per audio frame basis and on a per frequency bin basis. In other words, the anti-noise is suppressed (e.g., deactivated) only in time frames and frequency bins (of the external microphone signal) that have been detected to be speech (as opposed to non-speech.) Note here that the VAD need not be a binary decision (speech/non-speech); it could instead be a speech presence probability according to which the anti-noise is varied with finer granularity (than just a binary decision.)

The speech-responsive approach described above (that adjusts the anti-noise responsive to detecting speech on a per audio frame basis) may be augmented by adjusting how the ambient sound is being reproduced. Whenever speech is detected in a given audio frame, the ambient sound is filtered with more gain in a high frequency band than in a low frequency band. At the same time, the anti-noise may be maintained at a greater level in the low frequency band than in the high frequency band. The latter may be in addition to the anti-noise being adjusted on a per frequency bin basis responsive to the speech detection.

Figure 6:
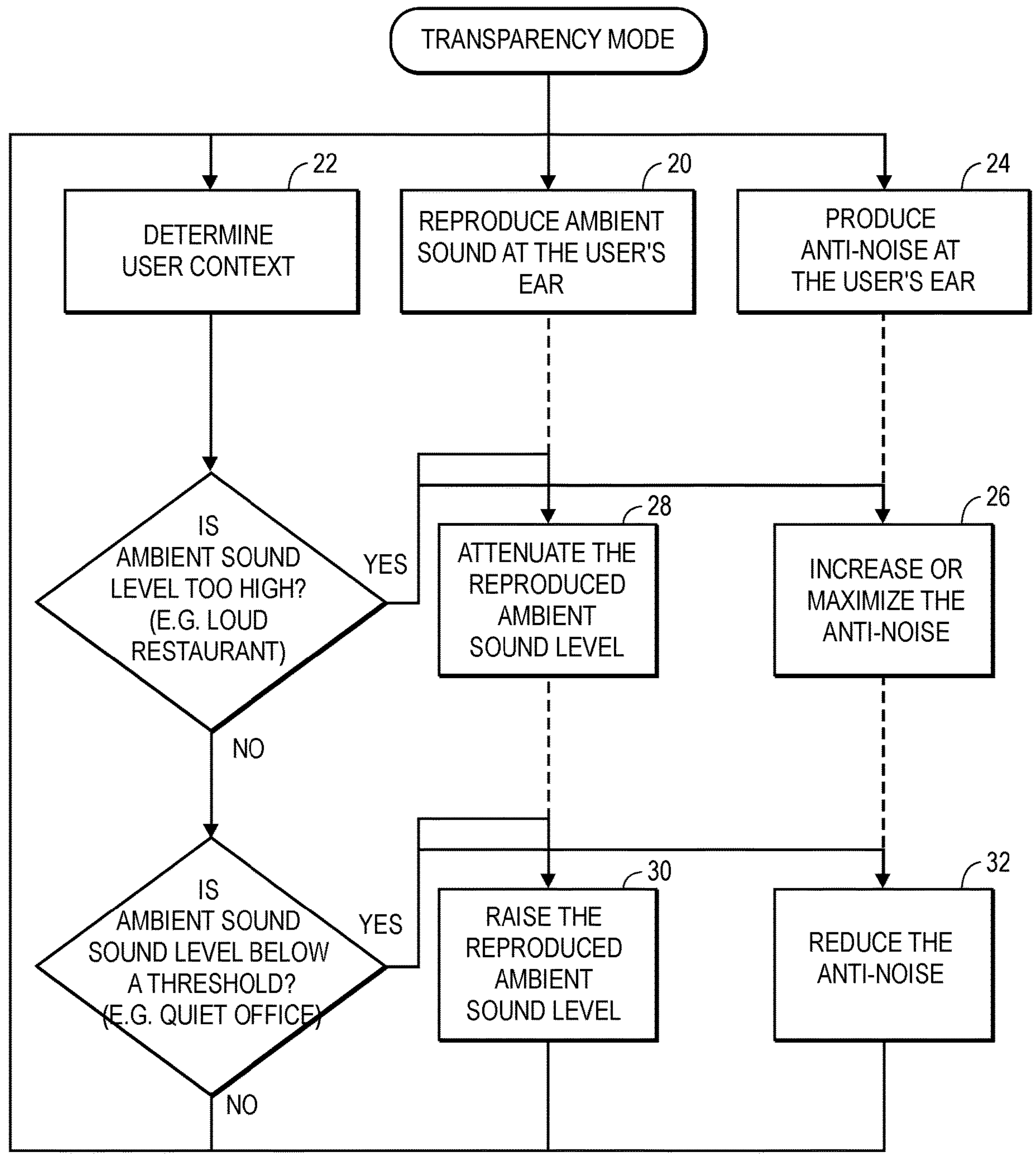
FIG. 6 is a flow diagram of method for ambient sound enhancement when ANC is available, to turn down the ambient as heard by the user.

In one aspect, referring now to the flow diagram of FIG. 6, the audio system may be adapted not to maximize acoustic cancellation (of the ambient sound that has leaked past the audio device into the user's ear) but rather to operate in transparency mode based on having determined a wearer context that suggests "turning down" what is being heard by the user. This process may or may not involve compensating for the users hearing loss. The process begins where, in transparency mode, the Gase block as seen in FIG. 2 is applying some gain to the ambient sound pickup channel, in order to overcome occlusion of the wearer's ear due to the audio device, so that the wearer can hear the reproduced ambient sound through the ASE filter 6 path (operation 20.) While performing operation 20, the process determines user context of the user automatically or without instruction from the user (operation 22.)

The user context encompasses any one or more the following. In one aspect, the determined user context discriminates between different types of ambient sound environments in which the wearer can find themselves, e.g., a concert, a public transport arena, a loud social gathering at a restaurant, in a coffee shop, in an office, and outdoors. The determination can be made by digitally processing a variety of input data, in real time. The input data may include an ambient sound pickup channel (from one or more microphones in the against the ear audio device or in a smartwatch being worn by the wearer, including a beamforming sound pickup channel), speech pickup via a vibration sensor, e.g., an accelerometer that is embedded in the headphone and is responding to bone conduction of the wearer's own voice, and sensor data from a variety of other types of sensors including time of day, and user location using a global positioning system or radio frequency triangulation. The input data may be processed to, for example, determine that the wearer is walking, running sitting, driving, or riding in a car, bus, train or boat, or is at a particular venue such as a train station or airport. The input data may also be processed to detect the type of ambient sounds that are being picked up, e.g., fire alarm, mechanical machine noise, city street sound, highway noise, construction site noise, train subway noise, babble, nature sounds, television, etc. More generally, the determination of user context may be the result of processing the input data using machine learning tools.

Note that user context may be determined automatically by the audio system (without instruction by the user) during any one of several operating modes, e.g., transparency, attenuated transparency, and active ear plug, as also described below The context determined in operation 20 may coincide with operation 24 in which the ANC block 10 may or may not be producing an anti-noise signal; also, the Ganc block may be attenuating but not eliminating entirely the anti-noise at its output (depending upon its gain setting.) Now, as part of or a result of the user context determination, if the ambient sound level is detected to be too high (by the ambient sound environment analyzer 8—see FIG. 2) then the Ganc block as seen in FIG. 2 may be signaled to perform no attenuation, or attenuate less, so as to produce more anti-noise (operation 26), thereby resulting in more cancellation of the ambient sound (quieter total sound level at the users ear.) Contemporaneously or alternatively, the system may signal the Gase block to attenuate the reproduced ambient sound (operation 28), e.g., by at least 20 dB in terms of amplitude gain that the Gase block is applying to the ambient sound pickup channel (detected ambient sound.) Together the two operations 26, 28 better protect the hearing of the wearer against a loud environment.

On the other hand, still referring to FIG. 6, if the determined user context in operation 22 indicates that the ambient sound level is below a threshold, such as in a quiet office, then operation 30 is performed in which the reproduced ambient sound is raised back up (its level is raised by increasing the gain that is being applied by the Gase block.) In addition, or alternatively, the anti-noise is reduced in operation 32 (by reducing the gain applied by the Ganc block which reduces the level of anti-noise but not entirely eliminating the anti-noise that is being produced.)

Although FIG. 6 shows two possible routes to take when determining user context, the solution more generally supports finer granularity: there may be more than two different user contexts (as described below using several examples) that lead to more than two ways of tuning the Gase block and the Ganc block. For example, there may be a user context that indicates an "intermediate" ambient sound level (between "quiet" or low ambient sound level, and "loud" or high ambient sound level) or a particular type of ambient sound environment such as "outdoors", that leads to a different combination of tuning the Gase block and the Ganc block. More generally, the audio system supports two or more user contexts each of which can be defined using any suitable combination of parameters such as detected ambient sound level, time of day, detected type of sound using a sound type classifier, ambient light level, user movement context such as walking, running, or driving, presence of wind, etc. And the responses to such user contexts may vary including tuning not just the Gase block and the Ganc block but also the ASE filter 6 in different ways (according to the particular user context.)

In another aspect of the transparency mode, the system enhances spectral flatness of the reproduced ambient sound whenever the system determines a certain user context, e.g., "wearer is at a concert." This may be achieved by appropriately shaping the filtering function of the Gase block. But when the wearer starts talking to someone at the concert, the determined user context changes, e.g., "wearer is talking with someone in their environment", because the system detects speech by another person in the environment and/or speech by the wearer, the Gase block is signaled to emphasize speech frequencies (e.g., by appropriately shaping the filtering function of the Gase block.) The frequency response in that case is no longer flat.

In yet another aspect of operating in transparency mode, the system reduces the transparency gain that it applies (in the Gase block), differently in different user contexts. For instance, when the determined context indicates that the wearer is "talking over" ambient noise, the transparency gain is reduced more than when the wearer is passively listening to their environment. This helps the wearer better understand or hear the speech of someone who is talking in the otherwise noisy environment.

In still another aspect, the wearer may be at a concert when during a lull in the performance the wearer starts talking to a friend next to them (who is also at the concert.) In that case, the audio system detects a drop in the ambient noise/sound level (below a threshold) and perhaps also a contemporaneous increase in speech activity. The speech activity may be either the wearer's own voice or that of the friend nearby. In response the system may reduce its anti-noise output (e.g., raise attenuation by Ganc), and perhaps increase its transparency gain Gase that it applies to an ambient sound pickup channel, and also perhaps emphasize the speech frequency range—this is also referred to as spectral shaping. When the concert performance resumes, the detected ambient sound level increases (above the threshold), in response to which the system resumes its focus on achieving spectral flatness of the reproduced ambient sound while still being ready to protect the wearers hearing by increasing anti-noise.

The operating modes of the audio system may include at least the following three modes: transparency (pass-through) mode; attenuated transparency mode; and active ear plug mode. Persons skilled in the art will appreciate that the system may include any suitable number of modes, and in some instances, there may not be discrete modes, but rather the audio system may seamlessly perform tuning based on current ambient sound conditions and, more generally, based on user context.

For purposes of explanation, the transparency mode may be referenced at or set to 0 dB, which is when the amplitude gain applied to the reproduced ambient sound is set just enough to overcome the passive attenuation that is due to the ear being occluded by the against the ear device such that the resulting sound output level is the same as if the wearer were not wearing the against the ear device. This gain may be higher for example in a high frequency band, if the user's hearing profile shows some high frequency hearing loss. The attenuated transparency mode may for example be set to −10 dB or other suitable level of attenuation that still allows some amount of transparency; the amplitude gain may be set in that case to for example enable the wearer to better hear someone talking in an otherwise noisy environment. The active ear plug mode (also referred to here as noise reduction mode or full ANC mode) is when maximum anti-noise is being produced to protect the wearer's hearing when the wearer's environment has become too loud. Note that such ANC may only be effective in cancelling ambient sound at lower frequencies, e.g., below 2 kHz, while passive attenuation due to simply wearing the against the ear device is effective at high frequencies, e.g., above 2 kHz.

Referring back to FIG. 4, this figure illustrates an example of two sound response curves (attenuation curves) that can be produced by the against the ear device, one that is due to active noise cancellation or active noise reduction (see FIG. 2 where the ANC block 10 and Ganc are together producing maximum anti-noise) and the other that is due to passive attenuation (due to occlusion of the ear by the against the ear device); the total amount of attenuation of the ambient sound (that is heard by the wearer) would be the sum of the two curves. Now, in cases where a flat response is desired at the wearer's ear (in contrast to the frequency dependent total attenuation curve), the ANC block 10 and/or its Ganc may be tuned to produce less anti-noise in the low frequency band (e.g., Ganc may be signaled to attenuate the anti-noise at its output) while at the same time raising the transparency gain (e.g., by signaling Gase to boost gain in the high frequency band but not in the low frequency band.) This transition between a flat response mode and the active ear plug mode in which the active noise cancellation should be maximized may be automatic (without user instruction needed) based on the wearer context which as described above may be determined by the ambient sound environment analyzer (FIG. 2.)

Figure 7:
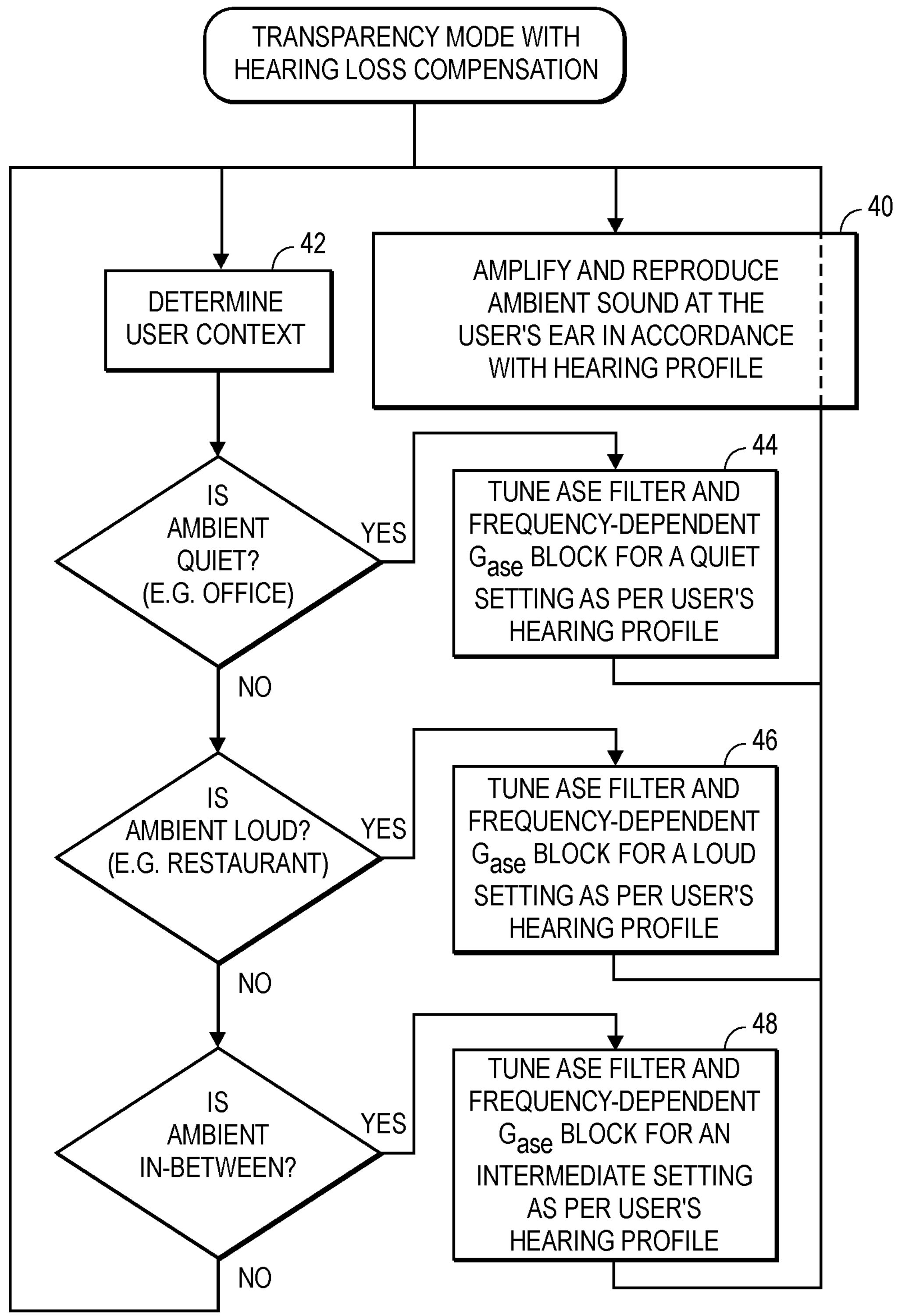
FIG. 7 is a flow diagram of a method for ambient sound enhancement based on parameters that define the user's hearing loss.

FIG. 7 is a flow diagram of a method for performing ambient sound enhancement based on the user's hearing loss—also referred to here as operating in transparency mode with hearing loss compensation. At a default setting, the detected ambient sound is amplified and reproduced at the user ear in operation 40, in accordance with the users hearing profile which in this case includes a hearing loss profile. Contemporaneously, user context is determined (operation 42) that leads to one of several routes for adjusting how the ambient sound is being reproduced. If the ambient is quiet, such as an office, the route takes operation 44 in which both the ASE filter 6 and the frequency dependent Gase block are tuned for a quiet setting as per the user's hearing profile. If the ambient is loud such a restaurant, the route takes operation 46 in which both the ASE filter 6 and the frequency dependent Gase block are tuned for a loud setting as per the user's hearing profile. And if the ambient is in between such outside or outdoors, the route takes operation 48 in which both the ASE filter 6 and the frequency dependent Gase block are tuned for an intermediate ambient noise level setting as per the user's hearing profile. While this method is illustrated in FIG. 7 using three routes, in general there may be more than three different user contexts defined which lead to more than three different ways of tuning the ASE filter 6 and the Gase block.

One aspect of the disclosure described above is a method for speech-aware sound enhancement by an against the ear audio device that can produce anti-noise for acoustic noise cancellation, the method comprising: amplifying and reproducing ambient sound by an against the ear audio device in accordance with a hearing profile of a user of the against the ear audio device, wherein the ambient sound is in an acoustic environment of the against the ear audio device; while reproducing the ambient sound in a), detecting speech in the ambient sound; and while reproducing the ambient sound in a), producing anti-noise so long as no speech is detected in the ambient sound, and reducing a level of the produced anti-noise whenever speech is detected. Whenever speech is detected, the ambient sound is amplified with more gain in a high frequency band than in a low frequency band. While the ambient sound is being amplified with more gain in the high frequency band than in the low frequency band, the anti-noise is being produced at a greater level in the low frequency band than in the high frequency band.

Another aspect of the disclosure described above is an audio headset having acoustic noise cancellation capability, the audio headset comprising: a left headphone speaker; a right headphone speaker; a processor; and memory having stored therein instructions that configure the processor to a) drive the left or right headphone speaker so as to amplify and reproduce ambient sound in accordance with a hearing profile of a user of the headset, wherein the ambient sound is in an acoustic environment of the headset, b) while the ambient sound is being reproduced according to a), detect that the ambient sound changes from quiet to loud, and c) in response to detecting that the ambient sound changes from quiet to loud, drive the left or right headphone speaker to start producing anti-noise, or raise a level of existing anti-noise being produced by the left or right headphone speaker. The memory may have stored therein further instructions that configure the processor to, in response to detecting that the ambient sound changes from loud to quiet, drive the left or right headphone speaker to reduce the level of anti-noise being produced. The anti-noise being produced may be in a low frequency band and not in a high frequency band. While the ambient sound is loud, dynamic range of the reproduced ambient sound becomes smaller when the anti-noise starts or when the level of existing anti-noise is raised.

Yet another aspect of the disclosure here as described above is a method for automatic sound enhancement by an against the ear audio device, the method comprising: a) reproducing ambient sound by an against the ear audio device, wherein the ambient sound is in an acoustic environment of a user who is wearing the against the ear audio device, and wherein the ambient sound is filtered in accordance with a frequency dependent gain; b) while reproducing the ambient sound in a), detecting that the ambient sound changes from quiet to loud; c) in response to detecting that the ambient sound changes from quiet to loud, reducing the frequency dependent gain in accordance with a hearing profile of the user; and d) reproducing the ambient sound, by the against the ear audio device, as filtered in accordance with the reduced frequency dependent gain. In the case where the against the ear audio device produces anti-noise for acoustic noise cancellation, the method further comprises: producing anti-noise by the against the ear audio device during a); and in response to detecting that the ambient sound changes from quiet to loud, raising a level of the produced anti-noise during d). In one aspect, the changes in the level of the anti-noise are performed no faster than once per second. In another aspect, the frequency dependent gain comprises reduced gain in a high frequency band and not in a low frequency band.

As described above, one aspect of the present technology is the gathering and use of data available from specific and legitimate sources to determine user context and adjust how ambient sound is reproduced for the user. The present disclosure contemplates that in some instances, this gathered data may include personal information data that uniquely identifies or can be used to identify a specific person. Such personal information data can include demographic data, location-based data, online identifiers, telephone numbers, email addresses, home addresses, data or records relating to a user's health or level of fitness (e.g., vital signs measurements, medication information, exercise information), date of birth, or any other personal information including any hearing loss.

The present disclosure recognizes that the use of such personal information data, in the present technology, can be used to the benefit of users. For example, the personal information data can be used to deliver enhanced ambient sound reproduction in accordance with their preferences or to protect their hearing health.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominent and easily accessible by users, and should be updated as the collection and/or use of data changes. Personal information from users should be collected for legitimate uses only. Further, such collection/sharing should occur only after receiving the consent of the users or other legitimate basis specified in applicable law. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates aspects in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of allowing the enhanced ambient sound reproduction process to access their hearing loss profile or access their location.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing identifiers, controlling the amount or specificity of data stored (e.g., collecting location data at city level rather than at an address level), controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, the ambient sound enhancement functions can still tune the Gase and Ganc blocks and the ASE filter 6 without having to know the location of the user or that the user has any hearing loss.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, although not shown in FIG. 2, the microphone signal containing the ambient sound (from the external microphone 3) may be further processed by an equalization, EQ, filter which serves to spectrally shape the microphone signal, and by a nonlinear limiter (not shown), before being combined with the program audio. Similarly, the program audio may be filtered by an EQ filter (not shown) before being combined with the processed and Gase-filtered ambient sound content. The description is thus to be regarded as illustrative instead of limiting.

What is claimed is:

1. A method for sound enhancement by an against the ear audio device that can also produce anti-noise for acoustic noise cancellation, the method comprising:

producing an ambient sound signal from an external microphone so that a user of the against the ear audio device hears their environment while wearing the device;

determining user context of the user while the user is wearing the device, wherein the user context is determined automatically or without instruction from the user; and based on the determined user context, producing using the external microphone an anti-noise signal for acoustic noise cancellation, ANC, and combining the anti-noise signal with the ambient sound signal before together driving a speaker of the against the ear audio device, a) determining that the user context has changed in a first instance by detecting that ambient sound level is above a threshold and in response i) attenuating the ambient sound signal by reducing gain applied to the ambient sound signal while contemporaneously ii) raising a level of the anti-noise signal, and b) determining that the user context has changed in a second instance by detecting that ambient sound level is below the threshold and in response i) raising the ambient sound signal by increasing the gain applied to the ambient sound signal while contemporaneously ii) reducing the level of the anti-noise signal but still producing anti-noise.

2. The method of claim 1 wherein determining user context comprises detecting that ambient sound level is above a threshold, and wherein attenuating the ambient sound signal comprises reducing an amplitude gain that is applied to detected ambient sound, by more than 20 dB.

3. The method of claim 1 wherein determining user context indicates the user is at a concert, the method further comprising flattening a spectrum of the ambient sound signal in response to the user context being at the concert.

4. The method of claim 1 further comprising detecting speech and in response increasing gain of speech frequencies in the ambient sound signal.

5. The method of claim 4 further comprising attenuating the ambient sound signal in response to detecting speech.

6. A method performed by a system having an against the ear audio device, the method comprising:

reproducing sound of a wearer's environment in a pass-through mode via an ambient sound signal from an external microphone, wherein the pass-through mode is one of a plurality of operating modes;

attenuating the reproduced sound in an attenuated pass-through mode by reducing a gain that is applied to the ambient sound signal, while still allowing some reproduced sound to be heard by the wearer, wherein the attenuated pass through mode is one of the plurality of operating modes;

further attenuating the reproduced sound by further reducing the gain that is applied to the ambient sound signal while producing anti-noise via an anti-noise signal using the external microphone, and combining the anti-noise signal with the ambient sound signal before together driving a speaker of the against the ear audio device in an active ear plug mode to protect the wearer's hearing when the wearer's environment has become too loud, wherein the active ear plug mode is one of the plurality of operating modes; and transitioning the system between the plurality of operating modes in response to user context by a) determining that the user context has changed in a first instance by detecting that ambient sound level is above a threshold and in response i) attenuating the ambient sound signal and ii) raising a level of the anti-noise signal by increasing a gain that is applied to the anti-noise signal, and b) determining that the user context has changed in a second instance by detecting that ambient sound level is below the threshold and in response i) raising the ambient sound signal by increasing the gain applied to the ambient sound signal and ii) reducing the level of the anti-noise signal but still producing anti-noise.

7. An audio system for enhancing sound produced by an against the ear audio device, the audio system comprising:

a processor; and memory having stored therein instructions that configure the processor to drive a speaker of the against the ear audio device to reproduce ambient sound via an ambient sound signal from an external microphone in the against the ear audio device so that a user of the against the ear audio device hears their environment while wearing the device, determine user context of the user while the user is wearing the device, wherein the user context is determined automatically or without instruction from the user, and based on the determined user context, drive the speaker of the against the ear audio device to produce anti-noise for acoustic noise cancellation, ANC, of the ambient sound via an anti-noise signal using the external microphone, and combining the anti-noise signal with the ambient sound signal before together driving the speaker of the against the ear audio device, a) determine that the user context has changed in a first instance by detecting that ambient sound level is above a threshold and in response i) attenuating the ambient sound signal by reducing gain applied to the ambient sound signal while contemporaneously ii) raising a level of the anti-noise signal, and b) determining that the user context has changed in a second instance by detecting that ambient sound level is below the threshold and in response i) raising the ambient sound signal by increasing the gain applied to the ambient sound signal while contemporaneously ii) reducing the level of the anti-noise signal but not eliminating anti-noise.

8. The audio system of claim 7 wherein the processor determines user context by detecting that ambient sound level is above a threshold, and attenuates the ambient sound signal by attenuating an amplitude gain that is applied to the ambient sound signal by more than 20 dB.

9. The audio system of claim 7 wherein the memory has stored therein further instructions that configure the processor to drive the speaker to flatten a spectrum of the ambient sound signal in response to the user context being at a concert.

10. The audio system of claim 7 wherein the memory has stored therein further instructions that configure the processor to detect speech and in response a) increase gain of speech frequencies in the ambient sound signal, and b) reduce gain of other frequencies in the ambient sound signal.

* * * * *